US008032332B2

(12) United States Patent
Sakurai et al.

(10) Patent No.: US 8,032,332 B2
(45) Date of Patent: Oct. 4, 2011

(54) SEMICONDUCTOR INSPECTING APPARATUS

(75) Inventors: Yuichi Sakurai, Tokyo (JP); Tadanobu Toba, Yokohama (JP); Shuji Kikuchi, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 754 days.

(21) Appl. No.: 12/099,868

(22) Filed: Apr. 9, 2008

(65) Prior Publication Data
US 2008/0262760 A1    Oct. 23, 2008

(30) Foreign Application Priority Data

Apr. 11, 2007 (JP) .................. 2007-103814

(51) Int. Cl.
G06F 11/00 (2006.01)
G01R 31/00 (2006.01)
(52) U.S. Cl. ...................... 702/188; 714/738
(58) Field of Classification Search .................. 702/188, 702/108; 382/145, 149; 348/86, 92; 714/738, 714/741
See application file for complete search history.

(56) References Cited

U.S. PATENT DOCUMENTS
6,958,768 B1 * 10/2005 Rao et al. ................. 348/86

FOREIGN PATENT DOCUMENTS

| JP | 2002-223203 | 8/2002 |
|---|---|---|
| JP | 2003-308649 | 10/2003 |
| JP | 2003-308694 | 10/2003 |
| JP | 2004-228906 | 8/2004 |
| JP | 2005-286952 | 10/2005 |
| JP | 2006-067413 | 3/2006 |

OTHER PUBLICATIONS

"SerialLite Megacore Function User Guide", Altera Corp., http://www.altera.com/literature/ug/ug_sl.pdf, Aug. 2005 (especially refer to p. 3-8).
"Aurora Protocol Specification", Xilinx Inc., http://www.xilinx.com/aurora/aurora_protocol_member/aurora_protocol_spec_sp002.pdf, Jun. 2004 (especially refer to p. 56).

* cited by examiner

*Primary Examiner* — Bryan Bui
(74) *Attorney, Agent, or Firm* — Antonelli, Terry, Stout & Kraus, LLP.

(57) ABSTRACT

A semiconductor inspecting apparatus includes: a buffer memory whose width is matched to the greater of parallel bus width and the width of the number of serial lanes; a preceding stage bus switching unit that fills the buffer memory with input data without making a free space; equivalent transmission capacity conversion including a following stage bus switching unit that fills read data to the width of an arbitrary number of serial lanes without making a free space; a preceding stage bus switching unit that fills a buffer memory with input data without making a free space; and equivalent transmission capacity inverse conversion including a following stage bus switching unit that fills a parallel bus of arbitrary width with data read from a buffer memory without making a free space.

12 Claims, 18 Drawing Sheets

F I G . 9
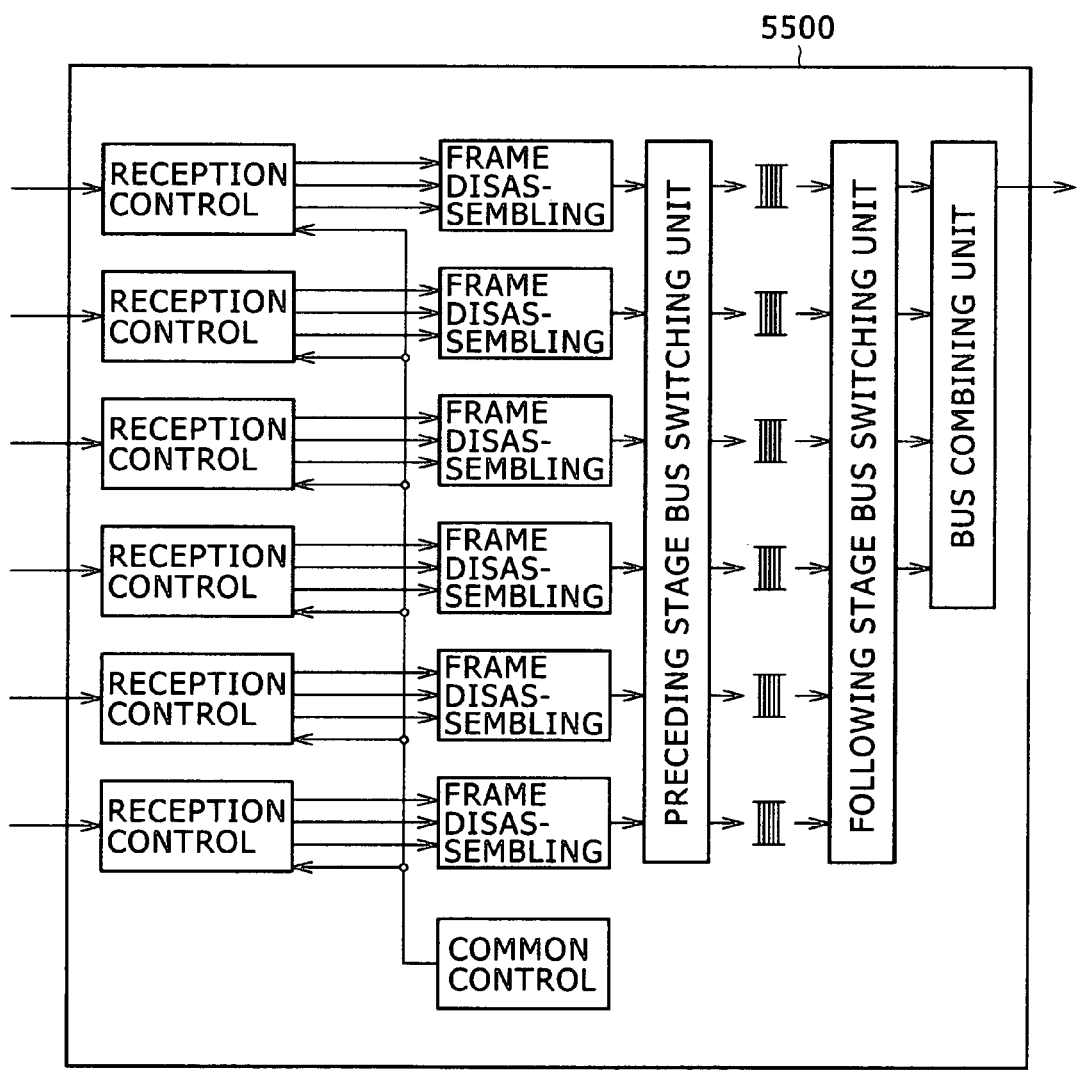

FIG.17

| CLOCK CYCLE | INPUT DATA | OUTPUT DATA |
|---|---|---|
| 1 | 32Bit: 0, 0 | 64Bit (empty) |
| 2 | 32Bit: 1, 1 | 64Bit: 0, 0 |
| 3 | 32Bit: 2, 2 | 64Bit: 0, 0, 1, 1 |
| 4 | 32Bit: 3, 3 | 64Bit: 2, 0, 2, 0, 1, 1 |
| ⋮ | | |

FIG.18

| CLOCK CYCLE | INPUT DATA | OUTPUT DATA |
|---|---|---|
| 1 | 96Bit (0,0,0,0,0,0) | 64Bit |
| 2 | 96Bit (...,0,0) | 64Bit (0,0,0,0) |
| 3 | 96Bit (1,1,1,1,1,1) | 64Bit (0,0) |
| ⋮ | | |

FIG.19

SEMICONDUCTOR INSPECTING APPARATUS

BACKGROUND OF THE INVENTION

The present invention relates to a semiconductor inspecting apparatus, and more particularly to a data transmission apparatus and a data transmission method in the semiconductor inspecting apparatus.

Because of the micronization of a today's semiconductor integrated circuit and the high density of substrate wirings, a circuit pattern formed on a semiconductor wafer is rapidly micronized. Accompanying with this, semiconductor inspecting apparatuses typified by a wafer appearance inspecting apparatus and a scanning electron microscope are demanded to have higher image processing power year by year. Accompanying with this, transmission capacity of image data increases, and higher data transfer speeds are desired. For example, as described in JP-A-2002-223203, in an apparatus typified by a wafer appearance inspecting apparatus and a scanning electron microscope, a huge amount of image data is serially transmitted from a transmitter to a receiver.

Recent semiconductor inspecting apparatuses are finding an increase in the size of imaging pixels and the type of inspection area size, and variations occur in the size of image data to be transferred. Besides a main image data transmission, the control system of an inspecting apparatus itself is increasingly complicated, and needs for the acquisition of monitoring data for debugging are also increasing.

Accompanying with this, within a semiconductor inspecting, many types of data transmission systems are required in terms of bus width and the magnitude of transmission capacity. To meet these needs, LSIs suitable for individual transmission systems have been individually developed and applied. Technologies for easily solving these needs are described in "SerialLite MegaCore Function User Guide", Altera Corporation, http://www.altera.com/literature/ug/ug_sl.pdf and "Aurora Protocol Specification", Xilinx Inc., http://www.xilinx.com/aurora/aurora_protocol_member/aurora_protocol_spec_sp002.pdf. These describe the binding of serial transmission control cores within a customizable LSI to achieve variable transmission capacity. Moreover, to flexibly respond to the magnitude of transmission capacity and bus width of transmission systems, general-purpose data transmission system technology having a width conversion mechanism is described in JP-A-2003-308694.

SUMMARY OF THE INVENTION

It is general to use high-speed serial data transmission apparatuses to transfer large-capacity image data at a high speed. The high-speed serial data transmission apparatuses often conventionally use existing serial transmission control circuit modules that can customize the number of serial lanes and transmission speeds. A problem in this case is that the bit width of a parallel bus is fixed every 16 bits. This is because a SERDES apparatus (parallel-serial converter) used in serial transmission control modules adopt an 8B/10B encode and decode method. The 8B/10B encode and decode method is an encode/decode method on a byte basis to take DC balance in serial transmission lines, and is widely used in serial data transmission. The DC balance indicates a deviation of the number of signals of '1' and '0' states on a serial transmission path. When it deviates to '1' or '0', a jitter component increases, and an increase in bit errors is caused. With the 8B/10B encode and decode method, eight-bit data of deviated DC balance such as "11110000" is converted into 10-bit data such as "0110110001" (or "1001001110"), with the effect that DC balance on a serial transmission path is stabilized and a bit error rate is decreased. When the 8B/10B encode is used, it is apparent that the unit of input/output data handled by one SERDES is eight bits. In existing modules such as SerialLite and Aurora, a parallel bus width interface is fixed to a size obtained by multiplying a byte width of each lane by the number of lanes. For example, the parallel bus width interface cannot be freely increased or decreased in size to meet constraints of hardware. As a result, when data transmission systems existing in a semiconductor inspecting apparatus are constituted by the number of serial lanes that achieves required transmission capacity, implementation by parallel bus width suitable for each of the data transmission systems becomes difficult, and application of a wide serial data transmission apparatus within the apparatus becomes difficult.

For individual transmission systems different in bus width and transmission capacity, there is a case where a specific serial data transmission apparatus is developed. In this case, however, there are a problem of an increase in new development costs, and a problem that reliability is not increased because data transmission apparatuses individually developed have different circuit constructions.

The present invention solves, in an apparatus including many types of data transmission systems different in required transmission capacity, a problem of a data transmission apparatus itself such as reduction in application scope due to the parallel bus width and the number of serial lanes that are fixed as described above, when the data transmission apparatus is installed in each transmission system, and a problem as the apparatus such as an increase in development costs and reduction in the reliability of transmission systems due to individual development of the data transmission apparatus, and provides a semiconductor inspecting apparatus that makes the data transmission systems within the apparatus common and is reduced in apparatus costs by realizing a data transmission apparatus and a data transmission method that have high freedom and are excellent in incorporation capability.

A principal disclosure of the present invention is a semiconductor inspecting apparatus is 1) a semiconductor inspecting apparatus including: a large-capacity data generation apparatus such as image sensor that images a wafer surface; and a data transmission apparatus including at least one of a data transmission control unit that controls the transmission of data generated by the large-capacity data generation apparatus and a data reception control unit that controls the reception of the data, wherein the data transmission control unit includes an equivalent transmission capacity conversion unit that equivalently converts data capacity transmitted from the large-capacity data generation apparatus, and a transmission control unit that transmits data transmitted from the transmission capacity conversion unit to the outside, wherein the data reception control unit includes a data reception control unit that receives data transmitted from the transmission control unit, and an equivalent transmission capacity inverse conversion unit that equivalently inverse-converts the data capacity transmitted from the data reception control unit, wherein the equivalent transmission capacity conversion unit includes a buffer memory matched to the greater of the parallel bus width of a parallel bus of arbitrary width specified by a first parameter or the width of an arbitrary number of serial lanes specified by a second parameter, a preceding stage bus switching unit that fills the buffer memory with input data from the parallel bus without making a free space, a following bus switching unit that fills data read from the buffer memory to the width of the arbitrary number of serial lanes without making a free space, and frame creation means for forming a serial transmission frame by using data read from the buffer memory, wherein the equivalent transmission capacity inverse conversion unit includes a buffer memory matched to the greater of the parallel bus width of a parallel bus or the width of the number of serial lanes, means for receiving reception frame data from the serial lanes and disassembles reception frames, the preceding stage bus switching unit that fills the buffer memory with input data from the parallel bus without making a free space, and the following bus switching unit that fills the parallel bus of arbitrary width with data read from the buffer memory without making a free space, wherein the data transmission apparatus includes an input unit that inputs the first parameter and the second parameter from the outside, and at least one of circuit modules that include the data transmission control unit and the data reception control unit that can set the parallel bus width and the number of serial lanes to a desired value, based on the first parameter and the second parameter inputted from the input unit.

Or, a principal disclosure of the present invention is a semiconductor inspecting apparatus is 2) a semiconductor inspecting apparatus including: a large-capacity data generation apparatus such as image sensor that images a wafer surface; a data transmission apparatus including at least one of a data transmission control unit that controls the transmission of data generated by the large-capacity data generation apparatus and a data reception control unit that controls the reception of the data; and a processing apparatus that processes the transmitted data, wherein the data transmission control unit includes a buffer memory matched to the greater of the parallel bus width of a parallel bus of arbitrary width specified by a first parameter and the width of an arbitrary number of serial lanes specified by a second parameter, bus switching means for filling the buffer memory with input data from the parallel bus without making a free space, bus switching means for filling data read from the buffer memory to the width of the arbitrary number of serial lanes without making a free space, and means for forming serial transmission frames by data read from the buffer memory, wherein the data reception control unit includes a buffer memory matched to the greater of the parallel bus width of a parallel bus of arbitrary width specified by a first parameter and the width of an arbitrary number of serial lanes specified by a second parameter, means for receiving reception frame data from the serial lanes and disassembles reception frames, bus switching means for filling the buffer memory with input data without making a free space, and bus switching means for filling the parallel bus of arbitrary width with data read from the buffer memory without making a free space, wherein the data transmission control unit and the data reception control unit each are constituted by circuit modules, and wherein each of the circuit modules has a program that has the first parameter, the second parameter, and a terminal capable of inputting the use of transmission control and reception control, adjusts parallel width and the width of the number of serial lanes by the first parameter and the second parameter inputted from the terminal, respectively, according to the use of transmission control and reception control inputted from the terminal, determines whether the modules are required, or combines them, and automatically customizes the respective apparatuses of the data transmission control unit and the data reception control unit.

These and other objects, features and advantages of the invention will be apparent from the following more particular description of preferred embodiments of the invention, as illustrated in the accompanying drawings.

BRIEF DESCRIPTION OF THE DRAWINGS

FIG. 9 is a drawing showing a data reception control unit when a parallel bus is 64 bits wide and the bus of a serial transmission control apparatus is 96 bits wide;

FIG. 17 is a drawing showing sequences of input data and output data concerning bus width change when input is 32 bits and output is 64 bits;

FIG. 18 is a drawing showing sequences of input data and output data when input is 96 bits and output is 64 bits;

FIG. 19 is a drawing showing sequences of input data and output data when input is 96 bits wide and output is 64 bits wide.

DESCRIPTION OF THE PREFERRED EMBODIMENTS

In a semiconductor inspecting apparatus including various types of data transmission systems having different required transmission capacities, the object, without reducing an application range as a result of fixing parallel bus width and the number of serial lanes when mounting a data transmission apparatus in each transmission system, of making the data transmission systems within the apparatus common, and providing a semiconductor inspecting apparatus with reduced apparatus costs has been achieved without an increase in development costs by individual developments of the data transmission apparatuses and reduction in reliability of the transmission systems by using data transmission control apparatuses and data transmission systems that are characterized by equivalent transmission capacity conversion.

First Embodiment

An embodiment of a semiconductor manufacturing apparatus of the present invention will be described using a semiconductor inspecting apparatus as an example with reference to the accompanying drawings.

Semiconductor inspecting apparatuses include optical ones, SEM-type appearance inspecting apparatus, SEM length measuring apparatus, and the like. A data transmission apparatus in an inspecting is required to transmit a huge amount of image data obtained from image data acquiring means.

Figure 1:
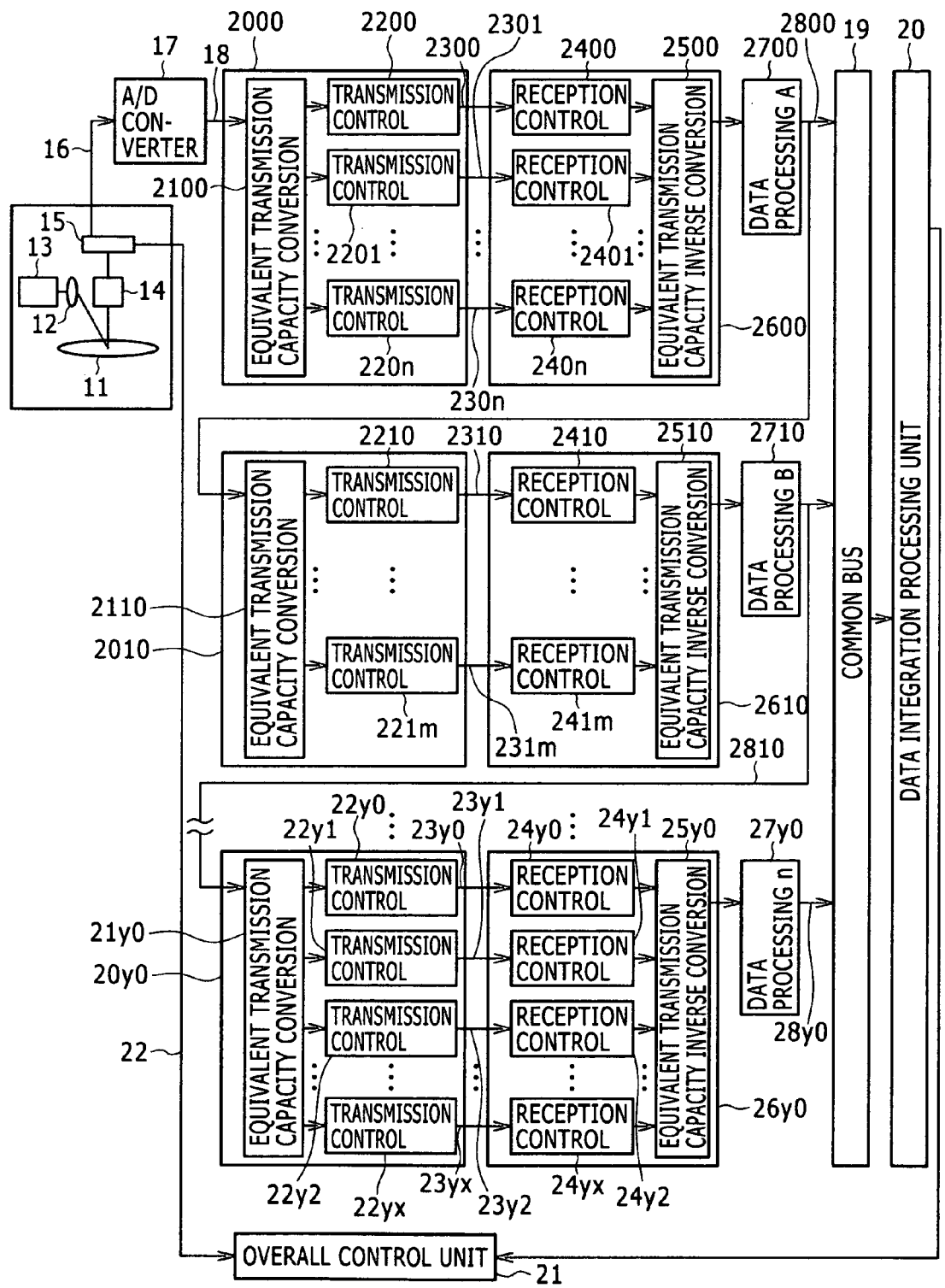
FIG. 1 is a schematic diagram showing one embodiment of an optical appearance inspecting apparatus.

FIG. 1 is a schematic diagram showing an embodiment of an optical appearance inspecting apparatus in an embodiment of a semiconductor manufacturing apparatus of the present invention.

Light (e.g., UV light, DUV light) emitted from a light source 13 is condensed in a slit shape by a condensing lens 12, and is irradiated onto a wafer 11 that moves to a specific direction through an objective lens.

Light reflected from a circuit pattern formed on the wafer is condensed by an objective lens 14, an image-formed circuit pattern is imaged by an image sensor 15 such as a TDI sensor, and image information 16 is outputted.

The image information is converted from analog quantity into digital information in an AD converter 17.

The digitalized image data 18 is sent to a data transmission control unit 2000. The image data, in the data transmission control unit 2000, is subjected to data conversion to match bus width of serial transmission control 2200, 2201, . . . , and 220n between the parallel bus 18 and equivalent transmission capacity conversion 2100. For example, when the parallel bus 18 is 64 bits wide, and three lanes are used as serial transmission lanes 2200, 2201, . . . , 220n, since the bus width of one lane is 16 bits, bus width in the whole serial transmission control is 46 bits. In short, the equivalent transmission capacity conversion 2100 converts a 64-bit bus into a 46-bit bus.

Data is transmitted using serial transmission lines 2300, 2301, . . . , 230n from the serial transmission control 2200, 2201, . . . , 220n to a data reception control unit 2600. The data reception control unit 2600 converts the transmitted serial data into parallel data in reception control 2400, 2401, . . . , 240n. The converted parallel data is converted into parallel bus data using an equivalent transmission capacity inverse converter 2500, and transmitted to a first data processor A 2700. Data 2800 processed here is sent to another data transmission control unit 2010 to perform next processing. The data transmission control unit 2010 and a data reception control unit 2610, like the data transmission control unit 2000 and the data reception control unit 2600 described previously, carry out equivalent transmission capacity conversion 2110 and equivalent transmission capacity inverse conversion 2510, perform data transmission, and perform data processing in a data processing apparatus B 2710. finally, after data transmission and data processing are terminated until data transmission control unit 20y0, data reception control unit 26y0, and data processor n 27y0, final image processing is performed based on individual results in a data integration processing unit 20 through a common bus 19, and a result is sent to an overall control unit 21.

FIG. 1 shows an example of a semiconductor inspecting apparatus to which a transmission apparatus of the present invention is applied.

Figure 4:
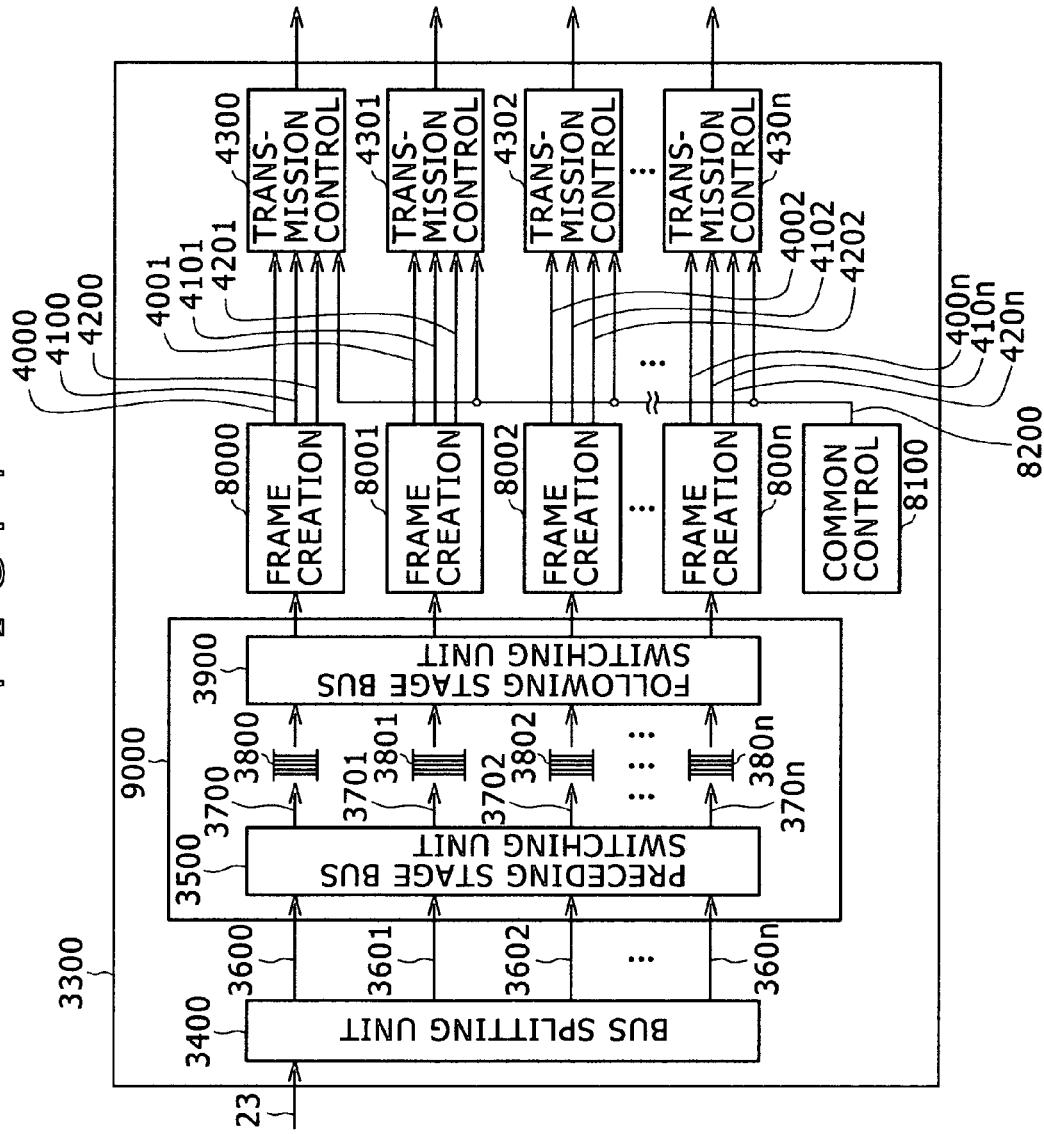
FIG. 4 is a drawing showing a data transmission control unit of the present invention.

FIG. 4 shows a data transmission control unit of the present invention. A bus splitting unit 3400 splits parallel bus input data 23 for each of the unit transmission widths in transmission control units 4300, 4301, 4302, . . . , 430n, a preceding stage bus switching unit 3500 distributes them to buffers 3800, 3801, 3802, 380n such as FIFO, a following stage bus switching unit 3900 distributes the split data equally to frame creating units 8000, 8001, 8002, . . . , 800n, the frame creating units 8000, 8001, 8002, . . . , 800n transform the data into transmission frames suitable for serial transmission, and the transmission control units 4300, 4301, 4302, . . . , 430n transmit the data. Here, equivalent capacity conversion is performed by including the preceding stage bus switching unit 3500, buffers 3800, 3801, 3802, . . . , 380n such as FIFO, a following stage bus switching unit 3900, and frame creating units 8000, 8001, 8002, . . . , 800n.

Figure 5:
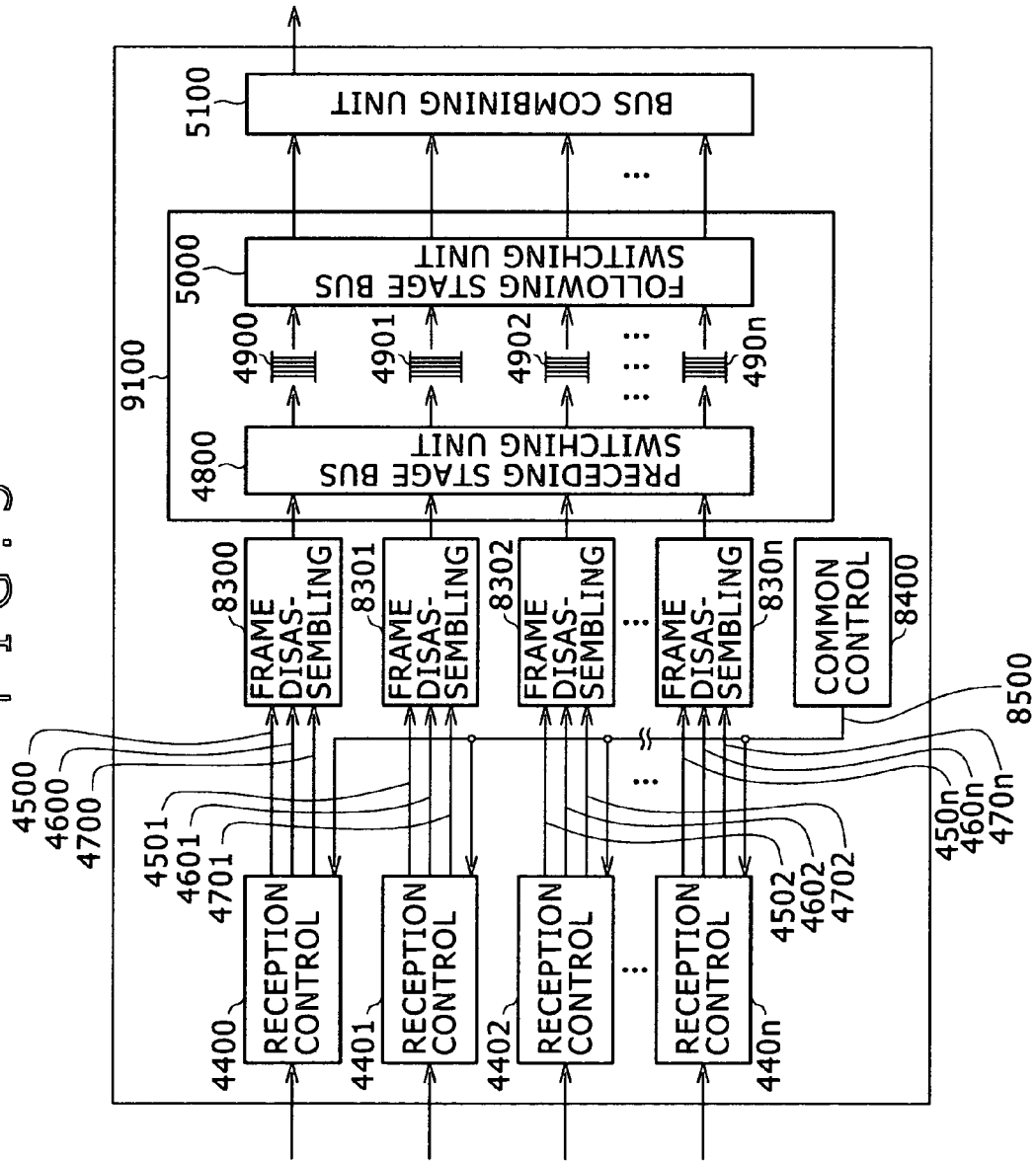
FIG. 5 is a drawing showing a data reception control unit of the present invention.

FIG. 5 shows the data reception control unit of the present invention.

Parallel data outputted from serial reception control units 4400, 4401, 4402, . . . , and 440n that receives serial data transmitted from the data transmission control unit is sent to frame disassembling units 8300, 8301, 8302, . . . , 830n, and transmission data is fetched from transmission frames. The fetched transmission data is inputted to a preceding stage bus switching unit 4800, bus switching processing is performed, and data is stored in buffers 4900, 4901, 4902, . . . , 490n such as FIFO. The data is combined in a bus combining unit 5100 via a following stage bus switching unit 5000. Here, equivalent capacity inverse conversion is performed by including the frame disassembling units 8300, 8301, 8302, . . . , 830n, the preceding stage bus switching unit 4800, buffers 4900, 4901, 4902, . . . , 490n such as FIFO, and the following stage bus switching unit 5000.

The present invention is applied to a semiconductor inspecting apparatus including a large-capacity data generation system such as an image sensor that images a wafer surface, a data transmission apparatus including a data transmission control unit and/or a data reception control unit, and a processor that processes transmitted data.

The data transmission control unit includes: a parallel bus of arbitrary width specified by a first parameter; any number of serial lanes specified by a second parameter; a buffer memory such as FIFO whose width is matched to the greater of parallel width and the width of the number of serial lanes; bus switching means for filling the buffer memory with input data from the parallel bus without making a free space; bus switching means for filling the width of the any number of serial lanes with data read from the buffer memory without making a free space; and means for constituting a serial transmission frame by data read from the buffer memory.

The data reception control unit includes: a parallel bus of arbitrary width specified by a first parameter; any number of serial lanes specified by a second parameter; a buffer memory such as FIFO whose width is matched to the greater of parallel width and the width of the number of serial lanes; means for receiving and disassembling frame data from the serial lanes; bus switching means for filling the buffer memory with input data without making a free space; and bus switching means for filling the parallel bus of arbitrary width with data read from the buffer memory without making a free space.

A data transmission control apparatus characterized by equivalent transmission capacity conversion is constructed by combining the data transmission control unit and the data reception control unit. The data transmission control unit and the data reception control unit are provided as a circuit module capable of using combinations of any parallel width and the number of serial lanes by duplicating them and changing parameters. The semiconductor inspecting apparatus is characterized in that the circuit module is used once or more in the data transmission control unit within the semiconductor inspecting apparatus.

For example, in the semiconductor inspecting apparatus shown in FIG. 1, the parallel input data 23 is split in the bus splitting unit 3400 for each of the unit transmission widths in the transmission control units 4300, 4301, 4302, . . . , and 430$n$, the preceding stage bus switching unit 3500 distributes the split data to buffers 3800, 3801, 3802, . . . , and 380$n$ such as FIFO, the following stage bus switching unit 3900 is used to distribute the data equally to frame creating units 8000, 8001, 8002, . . . , and 800$n$, the frame creating units 8000, 8001, 8002, 800$n$ transform the data into transmission frames suitable for serial transmission, and the transmission control units 4300, 4301, 4302, . . . , and 430$n$ are used for data transmission. The semiconductor inspecting apparatus includes the data transmission control unit that performs equivalent capacity conversion by including the preceding stage bus switching unit 3500, the buffers 3800, 3801, 3802, . . . , 380$n$ such as FIFO, the following stage bus switching unit 3900, and the frame creating units 8000, 8001, 8002, . . . , and 800$n$.

Parallel data outputted from the Serial receiving control units 4400, 4401, 4402, . . . , and 440$n$ that receives the serial data transmitted from this data transmission control unit is sent to the frame disassembling units 8300, 8301, 8302, . . . , and 830$n$, transmission data is fetched from transmission frames, the fetched transmission data is inputted to the preceding stage bus switching unit 4800 to perform bus switching processing, the data is stored in the buffers 4900, 4901, . . . , and 490$n$ such as FIFO, and the data is combined in the bus combining unit 5100 through the following stage bus switching unit 5000. The semiconductor inspecting apparatus includes the data reception control unit that performs equivalent capacity inverse conversion by including the frame disassembling units 8300, 8301, 8302, . . . , and 830$n$, the preceding stage bus switching unit 4800, the buffers 4900, 4901, . . . , and 490$n$ such as FIFO, and the following stage bus switching unit 5000.

The present invention relates to implementation of the data transmission control units that perform equivalent capacity conversion, and relates to the data transmission apparatuses, data transmission systems using them, and a semiconductor inspecting apparatus including them.

The above-described embodiment is an example of applying this patent to each of plural data transmission apparatuses having different required transmission capacities within the semiconductor inspecting apparatus.

According to this embodiment, in the case where, for example, a data transmission apparatus having 64-bit parallel bus input/output is included, when four serial lanes are conventionally required but required transmission capacity is satisfied with three serial lanes, by technology development of the present invention, by performing equivalent transmission capacity conversion from 64 bits to 46 bits, the number of relatively expensive serial transmission lanes can be decreased by one to enable transmission by three lanes, so that apparatus costs are reduced. For plural data transmission apparatuses, one verified circuit IP is duplicated, contributing to reduction in new development costs of a data transmission system and an increase in reliability.

The reason that the data transmission control units 2000, 2010, . . . , and 20$y$0 are separated from the data reception control units 2600, 2610, . . . , and 26$y$0 is that the data processors 2700, 2710, . . . , and 27$y$0 are mounted on substrates different from each other. Image data transmission by serial transmission requires no consideration of electrical mutual interference and skews between signals unlike bus connection, and can increase transmission speeds. Moreover, the serialization can significantly reduce the number of signal lines and reduce a wiring area, so that apparatus size can be easily miniaturized.

<Comparison with the Prior Art>

Items solved by the present invention are described below.

The data transmission control unit 2000, 2010, and 20$y$0, and the data reception control units 2600, 2610, . . . , and 26$y$0 are configured with conventional existing modules such as SerialLite and Aurora.

Figure 2:
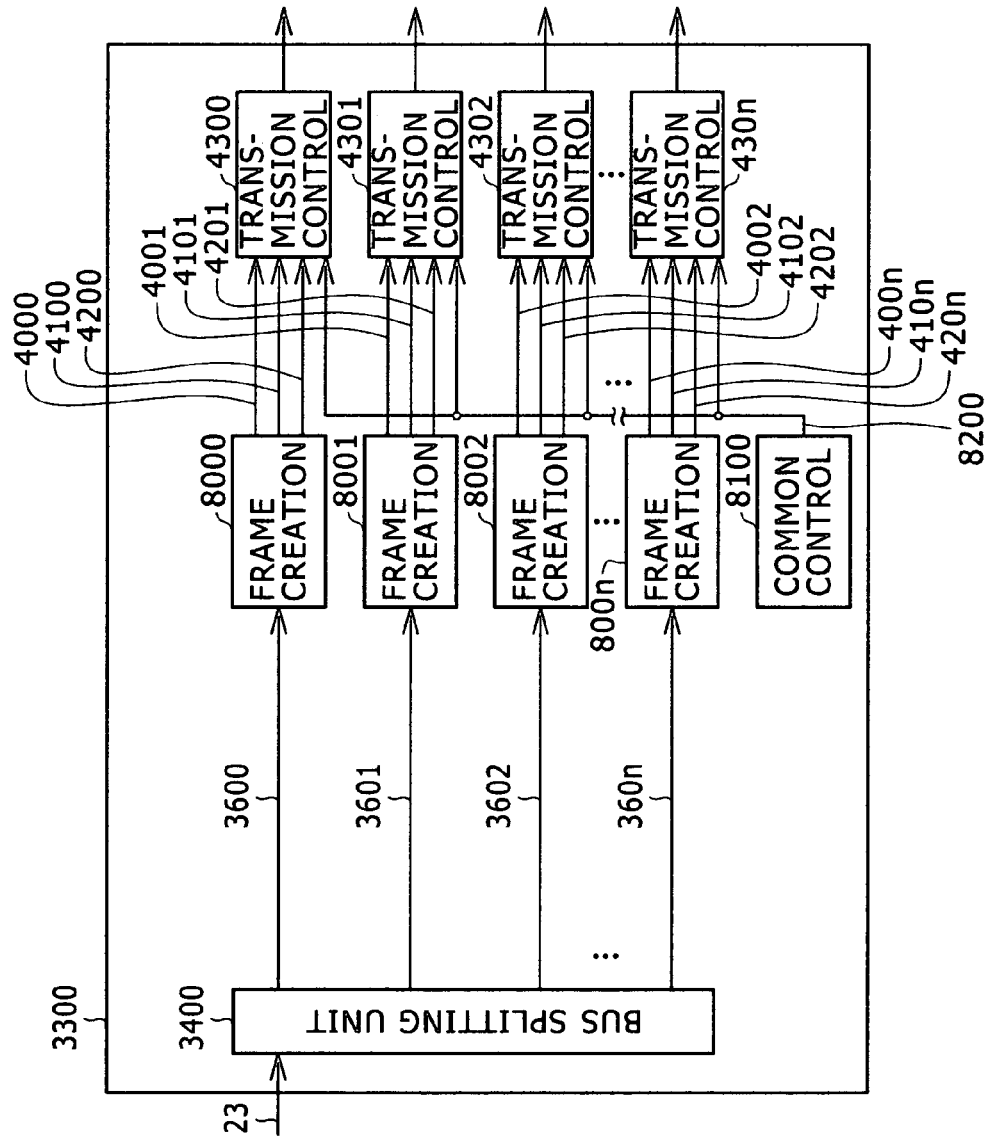
FIG. 2 is a drawing showing a conventional data transmission control unit.

FIG. 2 shows a conventional existing data transmission control unit 3300.

The parallel bus input data 23 is split in the bus splitting unit 3400 for each of unit transmission widths in the transmission control units 4300, 4301, 4302, . . . , and 430$n$, the split data is distributed equally to the frame creating units 8000, 800, 8002, . . . , and 800$n$, it is transformed into transmission frames suitable for serial transmission in the frame creating units 8000, 8001, 8002, . . . , and 800$n$, and the data is transmitted using the transmission control units 4300, 43001, 4302, . . . , and 430$n$.

Figure 3:
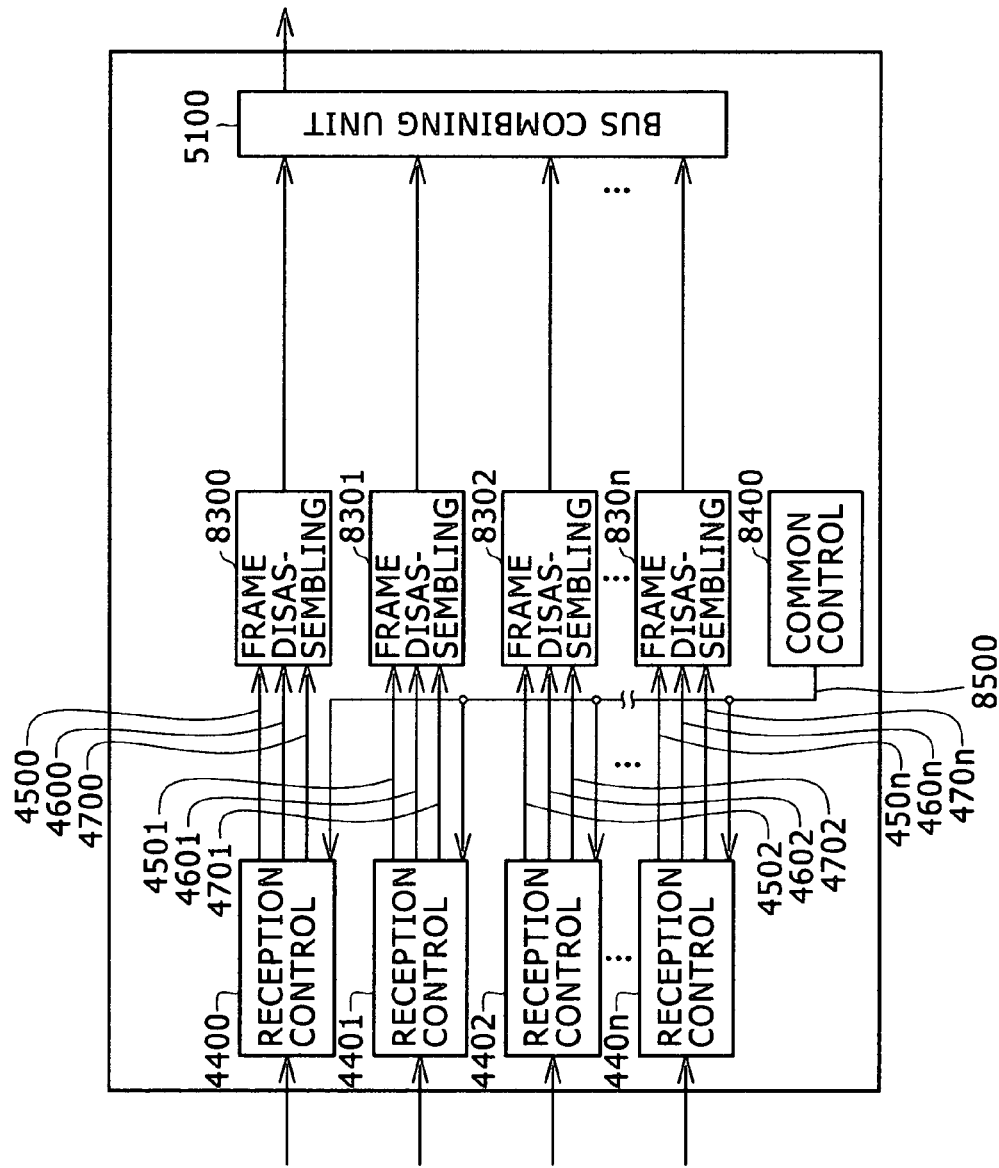
FIG. 3 is a drawing showing a conventional data reception control unit.

Likewise, FIG. 3 shows a conventional existing data reception control unit.

The data received through a serial transmission path is converted into parallel data in the serial reception control units 4400, 4401, 4402, . . . , and 440$n$, and sent as frame data to the frame data disassembling units 8300, 8301, . . . , and 830$n$. Transmission data fetched from the frames is combined in the bus combining unit 5100 and outputted to a parallel bus. A required transmission capacity and parallel width of output data 180 of the AD converter 17, and a required transmission capacity and parallel width of output data 2800 of the data processor A 2700 are often different. Likewise, required transmission capacities and parallel bus widths used in the data transmission control unit 20$y$0, the data reception control unit 26$y$0, and the data processor 27$y$0 are sometimes different from those of other data transmission control units and data reception control units.

In other words, in a semiconductor inspecting apparatus including plural data transmission control units, data reception control units, processors, and the like, because of differences in processing contents, image size to be used, and the like, required parallel width and transmission capacity are, in some cases, different among data transmission control units and data reception control units.

Transmission capacity and parallel bus width required by the output data 18 of the AD converter 17 may not perfectly match those achieved by the data transmission control unit 2000 and the data reception control unit 2600.

Likewise, transmission capacity and parallel bus width required by of the output data 2800 of the data processor A 2700 may not perfectly match those achieved by the data transmission control unit 2010 and the data reception control unit 2610. When these data transmission control units and data reception control units are replaced by conventional existing data transmission control units and data reception control units, a parallel bus width interface is fixed to the product of byte width of each lane multiplied by the number of lanes; the parallel bus width interface cannot be freely increased or decreased in size to meet the constraints of hardware. As a result, when data transmission systems existing in the semiconductor inspecting apparatus are constituted by the number of serial lanes to achieve a required transmission capacity, it becomes difficult to mount the data transmission systems with a parallel bus width suitable for each of them and it becomes difficult to apply a wide serial data transmission apparatus within the apparatus. For individual transmission systems different in bus width and transmission capacity, a specific serial data transmission apparatus may be developed. In this case, however, in addition to the problem of an increase in new development costs, there is a problem in that reliability does not increase because data transmission apparatuses individually developed have different circuit configurations.

<Change in Bus Width>

The following describes the processing of changing bus width which is the main theme of equivalent transmission capacity conversion and equivalent transmission capacity inverse conversion of the present invention. For bus width change processing, there is a problem to be solved. When the bus width of input and the bus width of output are the same or in the relation of a ratio of one to two or three to one, change of bus width from input to output can be achieved simply by using a bus switching circuit. Specifically, FIG. 17 shows a sequence 85 of input data and output data. Bus width is changed in the case where input data has 32 bits and output data has 64 bits. Input data is simply aligned to 64-bit width and outputted with a width of 64 bits. By repeating this, bus width conversion from input to output is enabled.

However, in plural transmission systems within the apparatus, the number of cases where the above can be achieved is small. In other words, when input is 96 bits and output is 64 bits, the relation of the widths of input and output is three to two, and when input data is fetched in one cycle in an output side, data of 32 bits remains in an input side without width conversion being performed. Data not subjected to the width conversion is put on an output bus in the next output cycle. In this case, only 32 bits of the next input data 96 bits flow to the output side, and the remaining 64-bit data remains again without width conversion being performed. When data remaining without width conversion being performed exists, an input bus cannot admit data and data input must be stopped, causing reduction in transmission capacity and complicating a control system. Specifically, FIG. 18 shows a sequence 86 of input data and output data. In an input side, in a cycle 2, input data 32 bits are left behind, and in the cycle 2, input data 1 cannot be inputted. In short, transmission capacity is reduced.

In other words, when the bus width of input and the bus width of output are not the same or not in the relation of a ratio of one to two or three to one, mere use of the bus switching circuit yields data remaining without width conversion being performed and disables width conversion.

For data transmission control circuits within the semiconductor inspecting apparatus of the present invention, in order that the bus widths of input and output can be freely set independently from each other, this problem had to be solved. For this problem, this time, equivalent capacity conversion is performed by including the preceding stage bus switching unit 3500, the buffers 3800, 3801, 3802, . . . , 380*n* such as FIFO, and the following stage bus switching unit 3900 within the data transmission control unit. Equivalent capacity inverse conversion is performed by including the preceding stage bus switching unit 4800, the buffers 4900, 4901, 4902, . . . , 490*n* such as FIFO, and the following stage bus switching unit 5000 within the data reception control unit.

The buffers are constructed in line with the greater of the widths of input bus and output bus, and a 16-bit wide buffer is defined as one unit.

This is because parallel bus width handled in SERDES incorporated in, for example, FPGA is often configured with 16 bits per lane.

Figure 8:
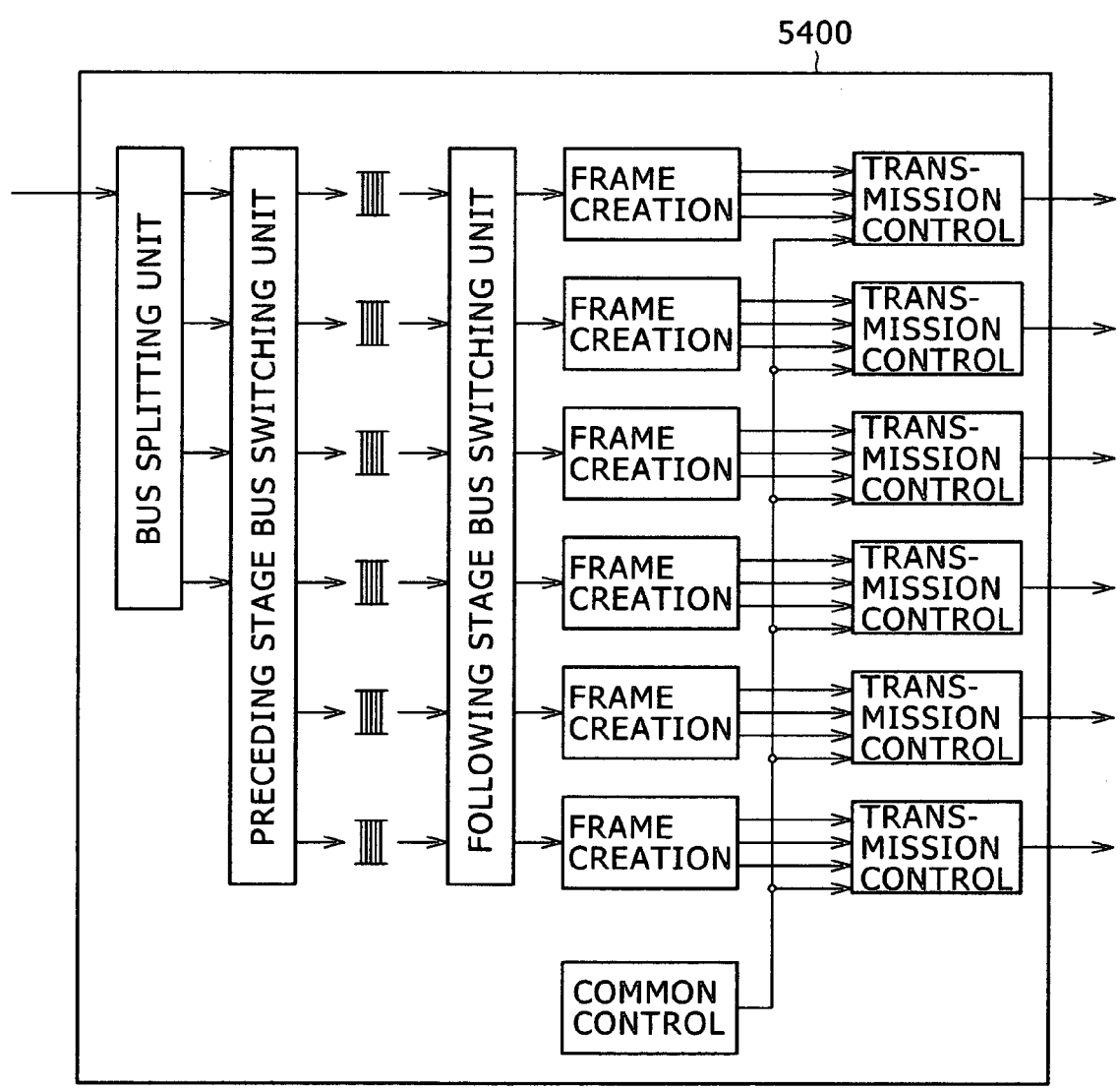
FIG. 8 is a drawing showing a data transmission control unit when a parallel bus is 64 bits wide and the bus of a serial transmission control apparatus is 96 bits wide.

For example, as shown in 5400 of FIG. 8, when input is 64 bit wide and output is 96 bits wide, six of this buffer are used and 96 bits wide.

<Need for Buffer>

The following describes the need to include the buffers 3800, 3801, 3802, . . . , 380*n* such as FIFO and the buffers 4900, 4901, 4902, . . . , 490*n* such as FIFO within the data transmission control unit. The descriptions differ depending on the relation of the respective bit widths of the preceding stage bus switching unit, the following stage bus switching unit, and the buffers. Therefore, specific examples are shown for description.

Figure 19:
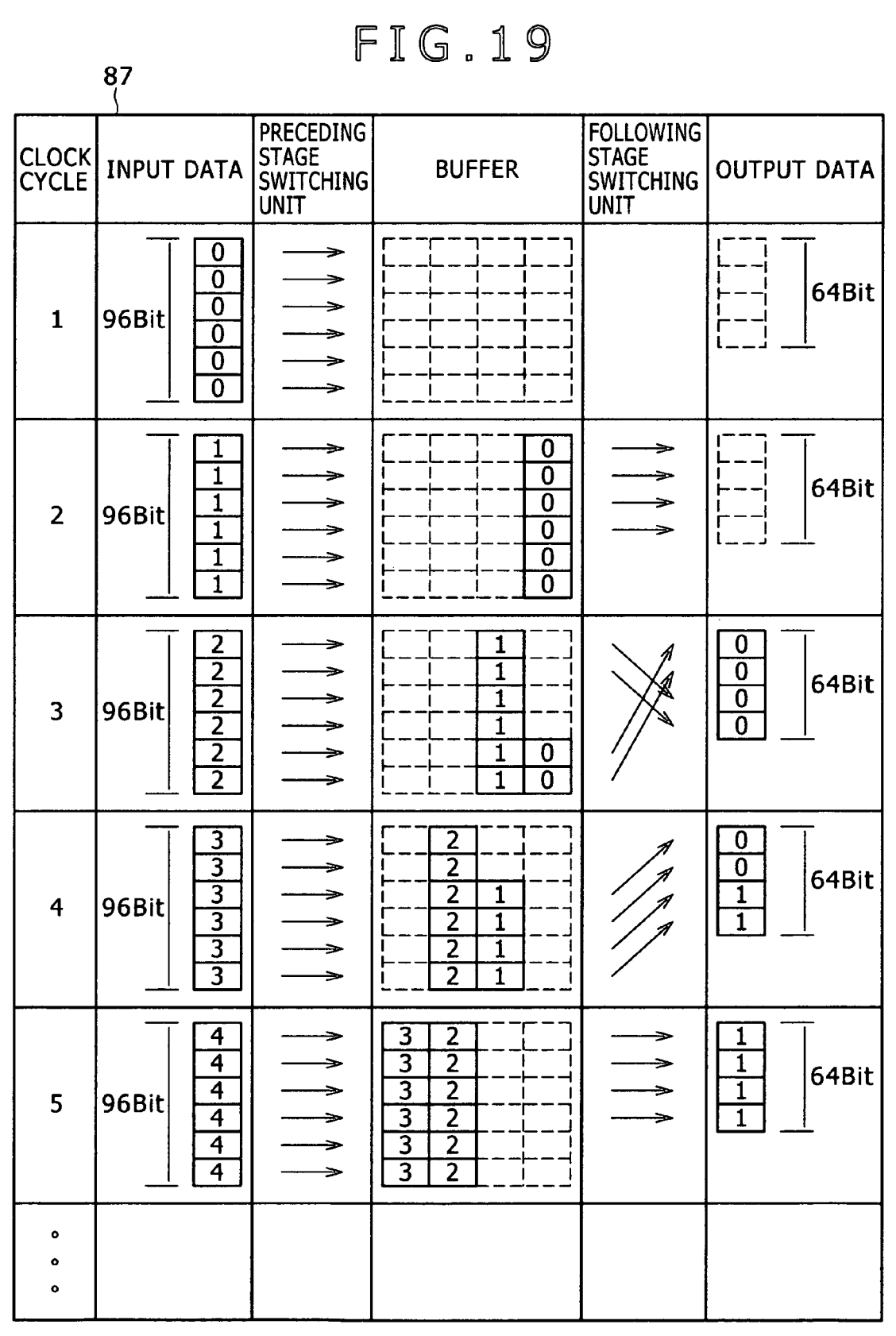

For example, the case where input is 96 bits wide and output is 64 bits wide is described using a sequence 87 of FIG. 19.

Six buffers are used and 96 bits wide.

In this case, the preceding stage bus switching unit performs no special processing because input bus width is the same as the bus width of the buffers, and input bus data is written to the buffer in each cycle.

The following stage bus switching unit, when fetching data from a buffer memory, fetches data of buffers of first to fourth indexes of a buffer memory with 64-bit width. Next, on confirming that data has been inputted from the input side to the buffer memory of fifth, sixth, first, and second indexes, the following stage bus switching unit fetches 64-bit wide data from the buffer memory of fifth, sixth, first, and second indexes. Next, on confirming that data has been inputted to the buffer memory of third, fourth, fifth, and sixth indexes, the following stage bus switching unit fetches 64-bit wide data from the buffer memory of third, fourth, fifth, and sixth indexes. After that, this processing is repeated.

Figure 20:
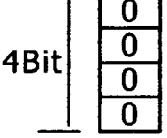
FIG. 20 is a drawing showing sequences of input data and output data when input is 64 bits wide and output is 96 bits wide.

The case where input is 64 bits wide and output is 96 bits wide is described using a sequence 88 of FIG. 20.

Six buffers are used and 96 bits wide.

The preceding stage bus switching unit, when writing data to the buffer memory, writes 64-bit wide data to the buffer of first to fourth indexes of the buffer memory. In the next cycle, it writes 64-bit wide data to the buffer memory of fifth, sixth, first, and second indexes. In the next cycle, it writes 64-bit wide data to the buffer memory of third, fourth, fifth, and sixth indexes. After that, this processing is repeated. Although the following stage bus switching unit simply fetches data from the buffer memory because the bus width of the buffer and the output bus width are the same, it performs output processing after confirming that data within the buffer has been filled to 96-bit width.

Specifically, the buffer is configured to exist between the preceding stage bus switching unit and the following stage bus switching unit. By this construction, when input is 96 bits and output is 64 bits, the widths of input and output are in the relation of a ratio of three to two, and when the output side fetches input data in one cycle, 32-bit data remains in the input side without being subjected to width conversion. However, since the data remains on the buffer and is not overwritten in the next cycle of the input side unlike flip-flops and the like, data input processing of the input side is not halted. Therefore, since a decrease in transmission capacity of the input side does not occur, and both the input bus and the output bus operate as usual, bus width conversion processing can be performed without complicating the control system.

Second Embodiment

The following describes the operation of the preceding stage bus switching unit 3500 and the following bus switching unit 3900 that are shown in FIG. 4, and the operation of the preceding stage bus switching unit 4800 and the following bus switching unit 5000 that are shown in FIG. 5. The preceding stage bus switching unit and the following bus switching unit are described using an example of performing ring-shaped bus switching processing.

Figure 10:
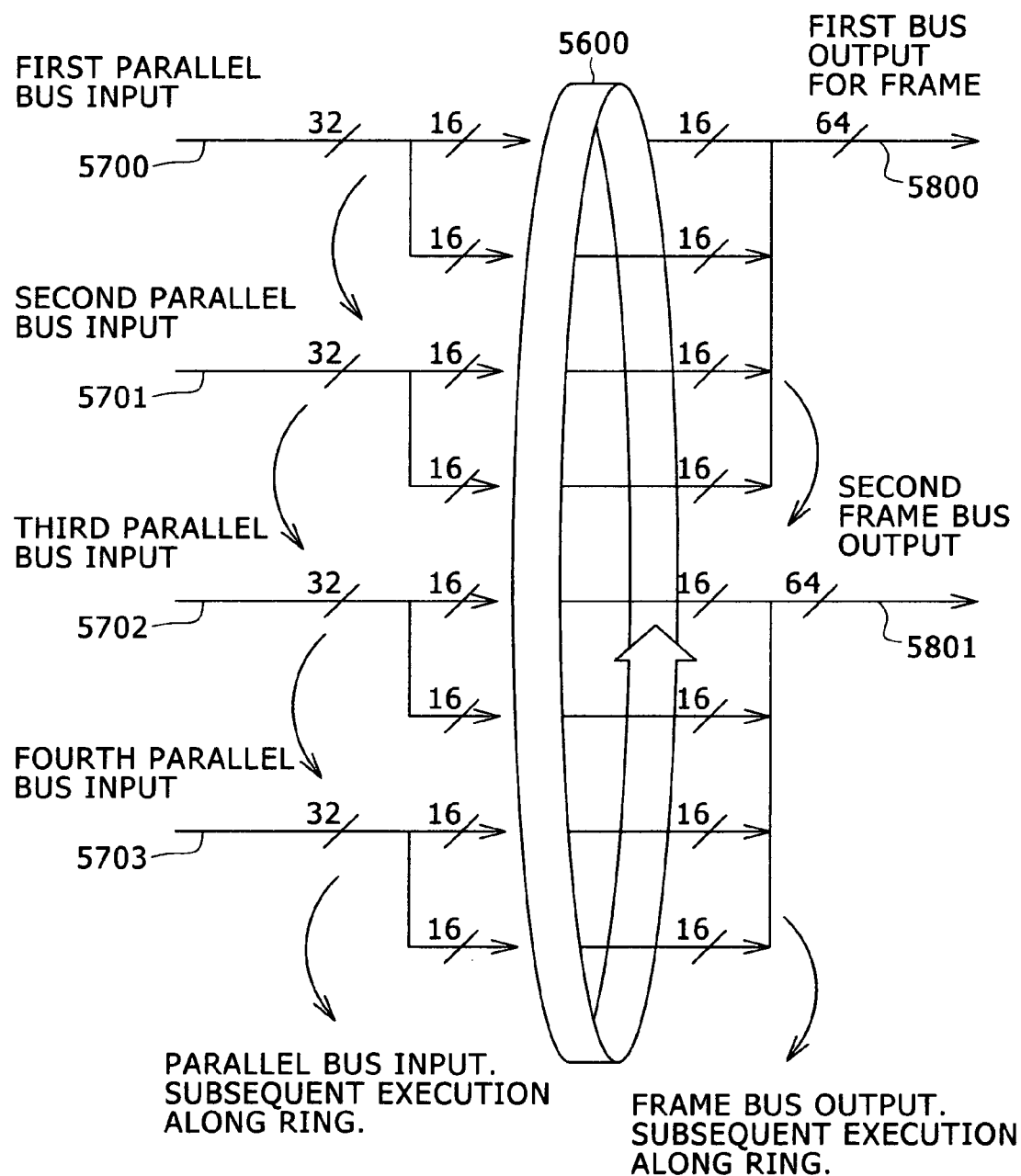
FIG. 10 is a drawing conceptually explaining the operation of ring-shaped width conversion.

FIG. 10 conceptually describes the operation of ring-shaped width conversion. On the left side, 32-bit wide data is inputted to a parallel bus. In first data input 5700, the data is split to two 16-bit data by bus splitting. Likewise, as in second data input 5701 and third data input 5702, for each input cycle, the data slides on the ring by the width of the parallel bus. It is assumed that a serial transmission control unit has four lanes and 64-bit width. When the second data input 5701 is completed at the parallel bus input side, 64-bit data 5800 is provided on the ring. The 64-bit data is used as data of first frame bus output. Subsequently, when input data of the parallel bus has been prepared as 64-bit data, frame bus output is performed. In the ring-shaped bus width conversion method, the clock speed of a side that inputs parallel data in ring shape, and the clock speed of a bus output side that outputs serial data from the ring shape do not necessarily match; any of them may be freely set.

It is apparent from the above-described brief description of operation that if the bus width of the parallel bus and the bus width of the frame bus output are an integer multiple of unit transmission bus width of the serial transmission control unit, the respective bus widths can be freely set within the range of an integer multiple of unit transmission bus width of the serial transmission control unit.

Figure 11:
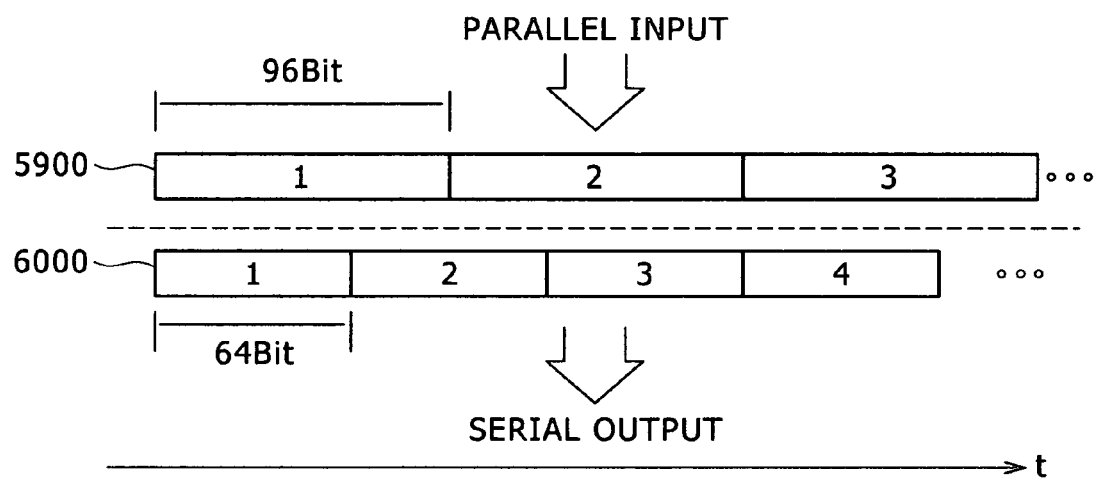
FIG. 11 is a drawing detailing actual data width conversion processing (parallel 96 bits, serial 64 bits) by use of a ring-shaped conversion circuit.
Figure 12:
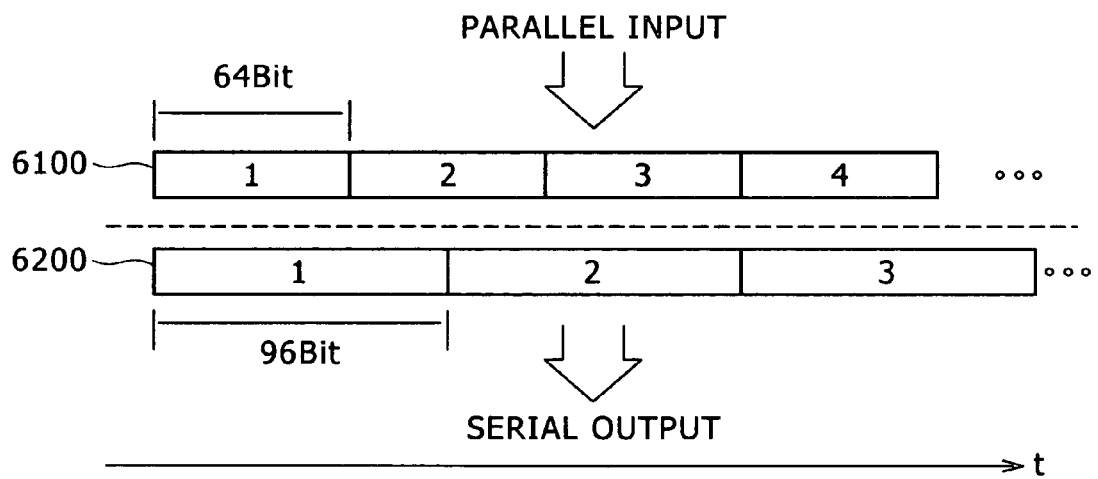
FIG. 12 is a drawing detailing actual data width conversion processing (parallel 64 bits, serial 96 bits) by use of a ring-shaped conversion circuit.

Details of actual data width conversion processing by use of the ring-shaped conversion circuit are given in FIG. 11 for parallel 96 bits and serial 64 bits, and in FIG. 12 for parallel 64 bits and serial 96 bits.

Third Embodiment

Figure 13:
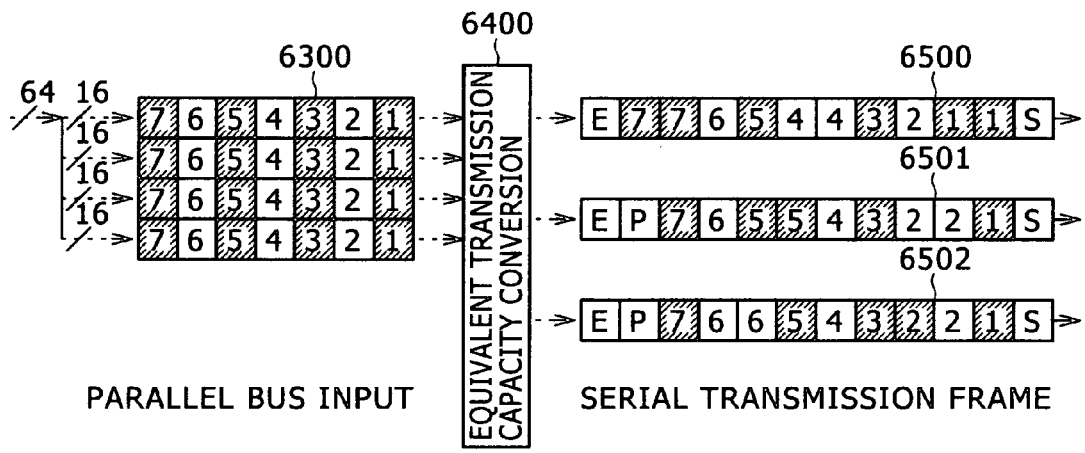
FIG. 13 is a drawing showing a serial transmission frame shape when transmission is performed with 64-bit width input and 46-bit bus width of a serial transmission side.

The shapes of serial transmission lanes generated by the equivalent transmission capacity conversion are shown in FIG. 13 on the assumption that three lanes are used with 64-bit width input and a serial transmission control unit bus width of 16 bits, and transmission is performed with a bus width of 46 bits. When seven-cycle data 6300 consisting of 64 bits is inputted from a parallel side, three transmission frames 6500, 6501, and 6502 are generated by equivalent transmission capacity conversion 6400. In the drawing, "S" designates the start of a frame, and "E" designates the end of a frame.

"E" indicates padding data added by the following stage bus switching unit, that is, invalid data. This is described below.

The following stage bus switching unit pads gaps of transmission data occurring during bus width conversion. In FIG. 13, when input is 64 bits and output is 46 bits, assume that 64-bit wide data is inputted in seven cycles. In this case, although the data is fetched as 46-bit data in nine cycles in an output side, in the next tenth cycle, only 16 bits remaining without width conversion being performed of seventh data of the input side are inputted and not filled to 46-bit width. In such a case, a serial transmission frame cannot be formed.

Therefore, the following stage bus switching unit generates special blank data for padding for the 32-bit blank data, and forms 96-bit data to form a serial transmission frame.

By performing the ring-shaped bus switching processing, unbalanced data transmission capacity after width conversion is suppressed. By the above processing, data inputted from the parallel bus achieves equivalent transmission capacity conversion by changing only bus width without changing transmission capacity. The equivalent capacity inverse conversion processing acquires original data by performing the reverse of the equivalent capacity conversion processing.

Fourth Embodiment

Figure 6:
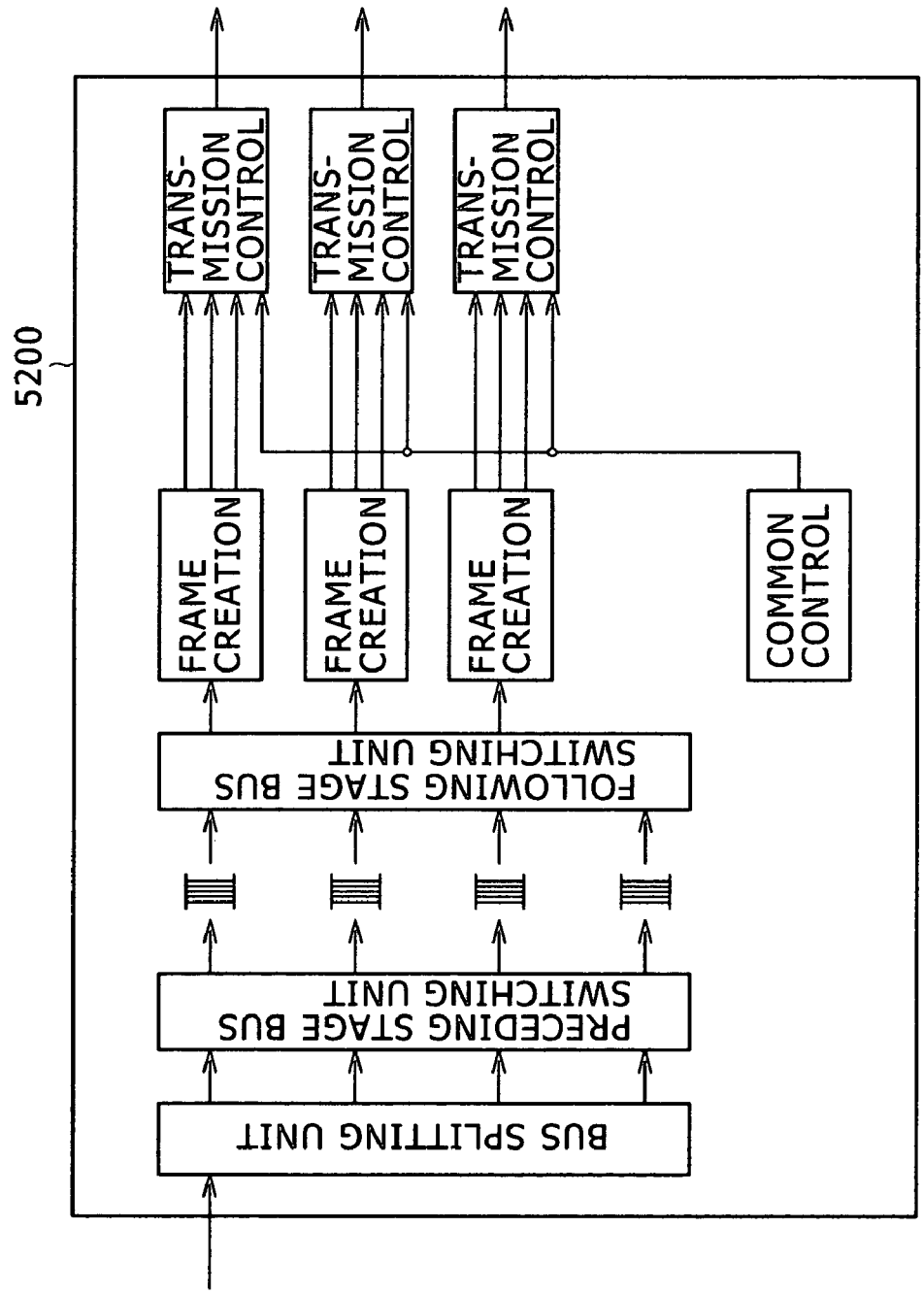
FIG. 6 is a drawing showing a data transmission control unit when a parallel bus bit width in a data transmission apparatus is wider than a bus bit width of a serial transmission control apparatus.
Figure 7:
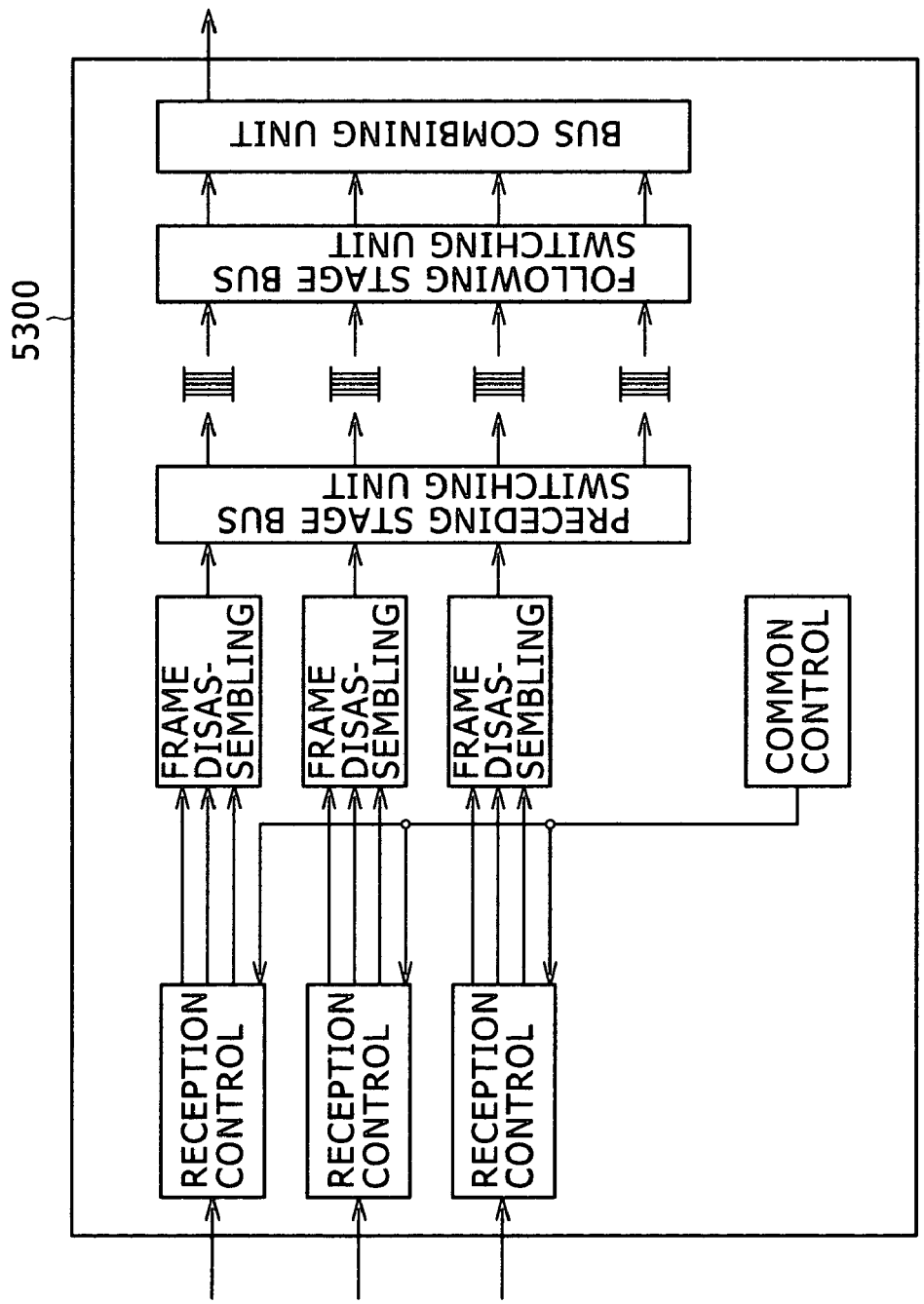
FIG. 7 is a drawing showing a data reception control unit when a parallel bus bit width in a data transmission apparatus is wider than a bus bit width of a serial transmission control apparatus.

The present invention can also apply to when parallel bit width in a data transmission apparatus is wider than the bus bit width of a serial transmission control apparatus. As an example, when a parallel bus is 64 bits wide, and the bus of a serial transmission control unit is 46 bits wide, the construction of a data transmission control unit is shown in 5200 of FIG. 6, the construction of a data reception control unit is shown in 5300 of FIG. 7, and frame shapes after width conversion are shown in FIG. 13.

In the present invention, frame data 6500, 6501, and 6502 of FIG. 13 having been subjected to equivalent transmission capacity conversion is always filled sequentially without gap with parallel bus data specified in a first parameter from the start of the frames. Thereby, an equivalent transmission inverse converter in a receiving side need only decode the data as parallel data for each first parameter from the start of received frames. By this construction, special wirings and hardware for equivalent transmission capacity conversion are not required between transmission and reception data transmission apparatuses of the present invention.

Fifth Embodiment

Figure 14:
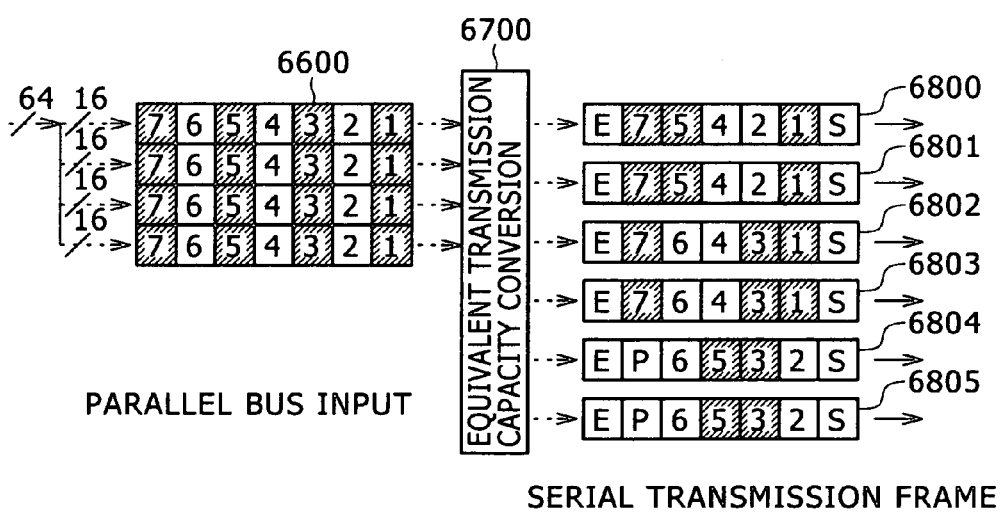
FIG. 14 is a drawing showing a frame shape when transmission is performed with parallel 64-bit width and bus 96-bit width of a serial transmission control apparatus.

As an example, when a parallel bus is 64 bits wide, and the bus of a serial transmission control unit is 96 bits wide, the construction of a data transmission control unit is shown in 5400 of FIG. 8, the construction of a data reception control unit is shown in 5500 of FIG. 9, and frame shapes after width conversion are shown in FIG. 14. As shown in the drawings, the present invention can also apply to when parallel bit width in a data transmission apparatus is narrower than the bus bit width of a serial transmission control apparatus.

In the present invention, frame data 6800, 6801, and 6802 of FIG. 14 having been subjected to equivalent transmission capacity conversion are filled sequentially without gap from the start of the frames without fail with parameter data specified in first parameters. Thereby, an equivalent transmission capacity inverse converter of a receiving side need only decode the frame data as parallel data for each of the first parameters from the start of the received frames. For this reason, special wirings and hardware for equivalent transmission capacity conversion are not required between transmission and reception data transmission apparatuses of the present invention.

Sixth Embodiment

Figure 15:
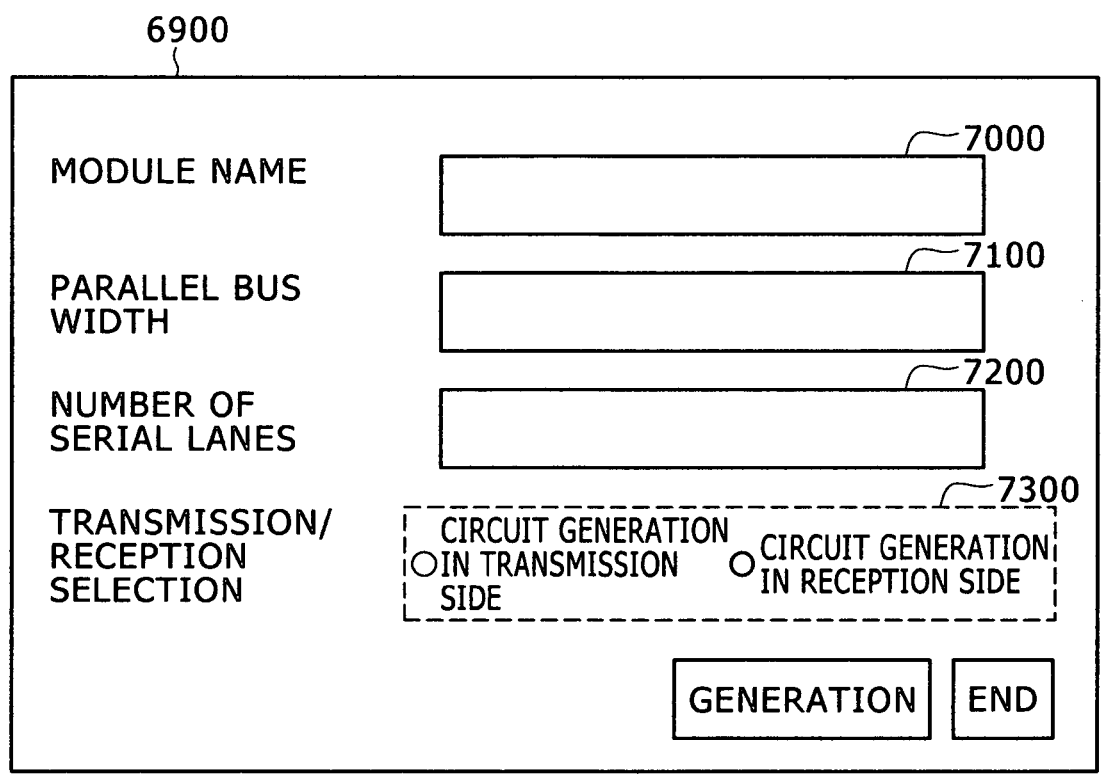
FIG. 15 is a drawing showing an example of automatic creation of each of a serial transmission control apparatus and a serial reception control apparatus by software on PC.

FIG. 15 shows an embodiment of automatic generation of a serial transmission control apparatus and a serial reception control apparatus of the present invention by software on a PC. A data transmission control unit includes: a parallel bus of arbitrary width specified by a first parameter; an arbitrary number of serial lanes specified by a second parameter; a buffer memory such as FIFO whose width is matched to the greater of a parallel bus width and the width of the number of serial lanes; bus switching means for filling the buffer memory without a free space with input data from the parallel bus; bus switching means for filling data read from the buffer memory to the width of the arbitrary number of serial lanes without making a free space; and means for constituting a serial transmission frame by data read from the buffer memory. A data reception control unit includes: a parallel bus of arbitrary width specified by a first parameter; an arbitrary number of serial lanes specified by a second parameter; a buffer memory such as FIFO whose width is matched to the greater of a parallel bus width and the width of the number of serial lanes; means for receiving frame data received from the serial lanes and disassembles the received frames; bus switching means for filling the buffer memory without a free space with input data from the parallel bus; and bus switching means for filling the parallel bus of arbitrary width without a free space with data read from the buffer memory. The data transmission control unit and the data reception control unit are provided in advance as separate circuit modules. In FIG. 15, a name 7000 for recognizing an apparatus as a general circuit module, a parallel bus bit width 7100 being a first parameter, the number of serial lanes 7200 being a second parameter, and transmission/reception generation circuit selection 7300 are arbitrarily set. Thereby, the circuit modules are selected and combined as required, and a bus width and the like are adjusted by the values of the first and the second parameters, so that the data transmission control unit and the data reception control unit that have been customized, and the respective apparatuses are automatically created. As a result, time costs such as manual rewriting of parameters of control apparatuses, and bugs such as setting mistakes can be eliminated.

Seventh Embodiment

Figure 16:
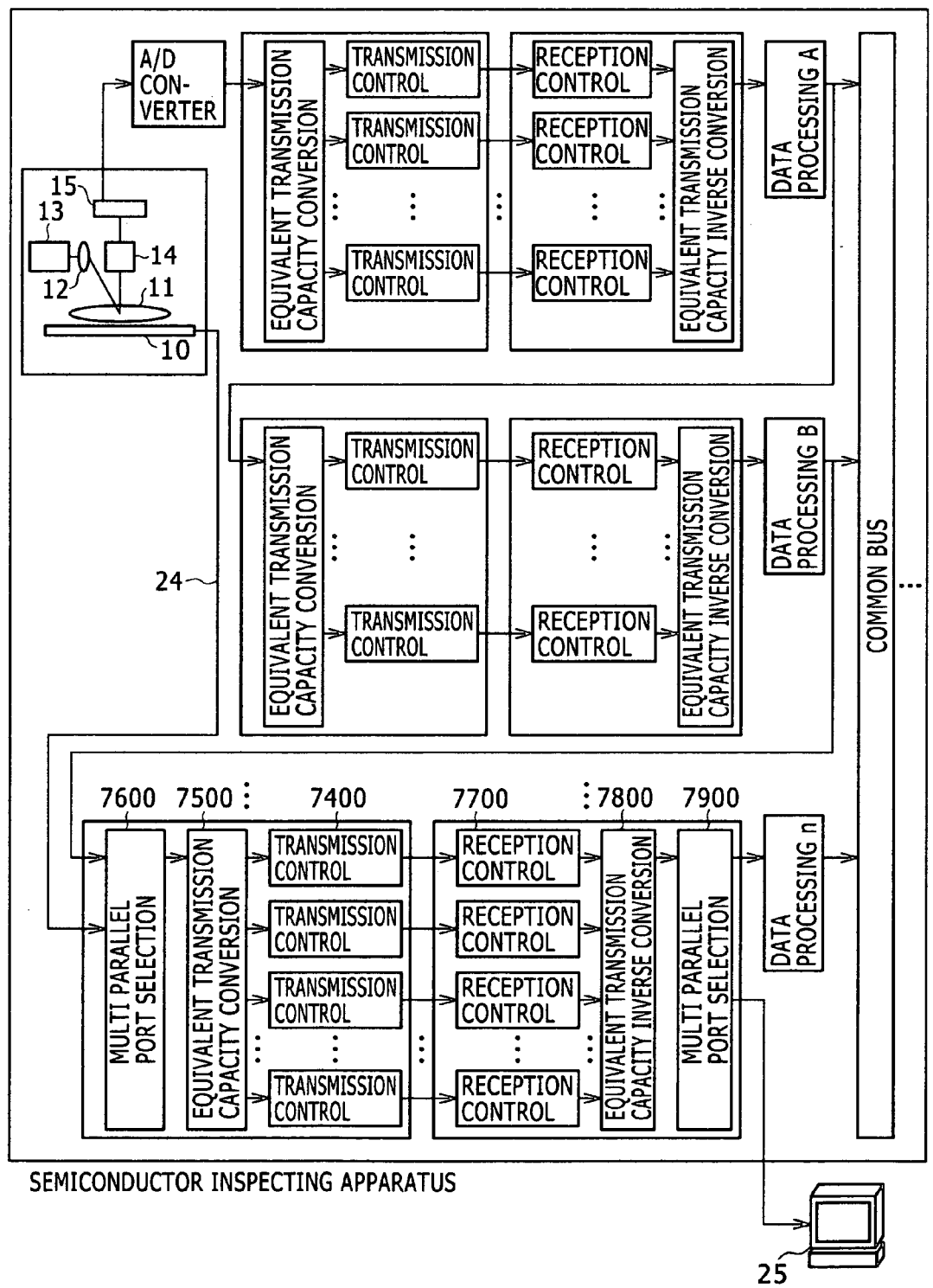
FIG. 16 is a drawing showing an example of transmitting large-capacity data such as image data and various measured data in a semiconductor inspecting apparatus by a single data transmission system.

As an embodiment of a transmission apparatus by the present invention, a large-capacity data transmission system such as image data in a semiconductor inspecting apparatus, and measured data, debug data, and the like occurring in an imaging apparatus such as a camera, and different locations of a stage control system that moves a wafer within a mirror body are transmitted in a single data transmission system by using a data transmission control apparatus in a transmitting side and a data transmission control apparatus in a receiving side that include plural parallel ports. This is shown in FIG. 16. An XY stage 10 is provided to move a wafer 11 on a mirror body. The stage measures its own position as required using laser light, and moves the wafer in X direction and Y direction while adjusting positional errors. For example, when the position measurement data 24 is outputted in an independent data transmission system, new transmission system development costs are required.

Here, according to the present invention, a multi-parallel port search 7600 that receives input from plural parallel ports is provided before an equivalent transmission capacity conversion 7500 of a transmission control apparatus of a serial transmitting side 7400. The multi-parallel port search 7600 can include plural parallel ports different in bus width and driving frequency, and always checks for the absence or existence of input data from all parallel ports. When data is inputted from a parallel port to be connected, it connects the parallel port and an input port of the equivalent transmission capacity conversion 7500.

A multi-parallel port selection 7900 is provided in the output of an equivalent transmission capacity inverse converter 7800 of a transmission control apparatus 7700 of a serial receiving side. The multi-parallel port selection 7900 checks frame data received in a serial reception control unit, determines which of all parallel ports connected to the output side of the multi-parallel port selection 7900 is to use the data, and connects the output of the equivalent transmission capacity inverse conversion 7800 and the selected parallel port. Debug data outputted from the XY stage 10 is port-selected in the parallel port search 7600 of the transmission control apparatus of a serial transmitting side 7400, converted in the equivalent transmission capacity conversion 7500, transmitted as serial data, subjected to the equivalent transmission capacity inverse conversion 7800 again on a receiving side, determined as debug data in the multi-parallel port selection 7900, and transferred to a PC 25 for processing debug data that exists outside the semiconductor inspecting apparatus. The debug data often has the extremely small required transmission capacity of one-tenth of that in a main image data transmission path. By using an existing transmission system for such a data transmission system of low required transmission capacity, data transmission is realized and low costs of the apparatus are achieved.

As has been described above, the present invention performs equivalent transmission capacity conversion that allows independent width setting for parallel buses and the number of serial lanes of a transmission apparatus, and independently settable, highly free combinations are possible with parallel buses and the number of serial lanes.

Moreover, the present invention has a mechanism of automatically generating circuit modules individually optimized by the setting of parallel bus width and the number of serial lanes by software so that the modules can be used with high reliability as circuit blocks having been operationally verified without requiring new development costs. Therefore, the present invention is effective for various apparatuses requiring plural data transmission systems that are different in parallel bus width, the number of serial lanes, and required transmission capacity.

According to the present invention, by including a data transmission control apparatus that performs parallel-to-serial equivalent transmission capacity conversion, and making parallel width and serial lanes independently customizable, independent and optimum combinations of input/output bus widths are achieved in contrast to conventional methods by which transmission capacity and input/output bus width are uniquely fixed.

Since the transmission apparatus is constructed by circuit modules that can be changed by parameters, identical circuit modules guaranteed in design quality can be changed by parameters and installed for plural data transmission systems within the semiconductor inspecting apparatus. Therefore, reduction in reliability and new development costs when individual transmission systems are newly developed are advantageously reduced.

Since serial lanes raising electrical mounting costs can be used by required transmission capacity for substrates and devices that are different in required transmission capacity in a semiconductor inspecting apparatus, cost reduction is realized.

The invention may be embodied in other specific forms without departing from the spirit or essential characteristics thereof. The present embodiment is therefore to be considered in all respects as illustrative and not respective, the scope of the invention being indicated by the appended claims rather than by the foregoing description and all changes which come within the meaning and range of equivalency of the claims are therefore intended to be embraced therein.

What is claimed is:

1. A semiconductor inspecting apparatus, comprising:
a large-capacity data generation apparatus that images a wafer surface;
a data transmission apparatus including at least one of a data transmission control unit that controls the transmission of the data generated by the large-capacity data generation apparatus and a data reception control unit that controls the reception of the data; and
a processing apparatus that processes the transmitted data,
wherein the data transmission control unit includes an equivalent transmission capacity conversion unit that equivalently converts data capacity transmitted from the large-capacity data generation apparatus, and a transmission control unit that transmits data transmitted from the equivalent capacity conversion unit to the outside,
wherein the data reception control unit includes a data reception control unit that receives data transmitted from the transmission control unit, and an equivalent transmission capacity inverse conversion unit that equivalently inverse-converts the data transmitted from the data reception control unit,
wherein the equivalent transmission capacity conversion unit includes:
a buffer memory having a parallel bus clock of arbitrary speed and a serial bus clock of arbitrary speed matched to a greater of parallel bus width having a parallel bus of arbitrary width driven by the parallel bus clock and specified by a first parameter and the width of the number of serial lanes having the serial lane of arbitrary number driven by the serial bus clock and specified by a second parameter;
a preceding stage bus switching unit that fills the buffer memory with input data from the parallel bus without making a free space;
a following stage bus switching unit that fills data read from the buffer memory to the width of the number of serial lanes of arbitrary number without making a free space; and
frame creation means for forming serial transmission frames by using data read from the buffer memory,
wherein the equivalent transmission capacity inverse conversion unit includes:
a buffer memory matched to the greater of the parallel bus width or the width of the number of serial lanes;
means for receiving reception frame data from the serial lanes and disassembles reception frames;
a preceding stage bus switching unit that fills the buffer memory with input data without making a free space; and
a following stage bus switching unit that fills data read from the buffer memory to a parallel bus of arbitrary width without making a free space, and
wherein the data transmission apparatus includes at least one of circuit modules that include an input unit inputting the first parameter and the second parameter from the outside and the data transmission control unit and the data reception control unit that can set the parallel bus width and the number of serial lanes to a desired value, based on the first parameter and the second parameter inputted from the input unit.

2. The semiconductor inspecting apparatus according to claim 1,
wherein the data transmission control unit, when the parallel bus width and the width of the number of serial lanes are not in a divisible relation, and the parallel bus width specified by the first parameter is smaller than the bus width of the number of serial lanes specified by the second parameter, enables equivalent transmission capacity conversion without reducing transmission capacity by storing data remaining without bus width conversion being performed that occurs in the preceding stage bus switching unit when filling the buffer memory with input data transmitted from the parallel bus without making a free space by the preceding stage bus switching unit to perform bus width conversion, in a buffer memory provided between the preceding stage bus switching unit and the following stage bus switching unit.

3. The semiconductor inspecting apparatus according to claim 1,
wherein the data transmission control unit, when the parallel bus width and the width of the number of serial lanes are not in a divisible relation, and the parallel bus width specified by the first parameter is greater than the bus width of the number of serial lanes specified by the second parameter, enables equivalent transmission capacity conversion without reducing transmission capacity by storing data remaining without bus width conversion being performed that occurs when filling data read from the buffer memory by the width of the serial lanes without making a free space by the following stage bus switching unit to perform bus width conversion, in a buffer memory provided between the preceding stage bus switching unit and the following stage bus switching unit.

4. The semiconductor inspecting apparatus according to claim 1,
wherein the data reception control unit, when the parallel bus width and the width of the number of serial lanes are not in a divisible relation, and the parallel bus width specified by the first parameter is smaller than the bus width of the number of serial lanes specified by the second parameter, enables equivalent transmission capacity conversion without reducing transmission capacity by storing data remaining without bus width conversion being performed that occurs when filling data read from the buffer memory by the width of the parallel bus without making a free space by the following stage bus switching unit to perform bus width conversion, in a buffer memory provided between the preceding stage bus switching unit and the following stage bus switching unit.

5. The semiconductor inspecting apparatus according to claim 1,
wherein the data reception control unit, when the parallel bus width and the width of the number of serial lanes are not in a divisible relation, and the parallel bus width specified by the first parameter is greater than the bus width of the number of serial lanes specified by the second parameter, enables equivalent transmission capacity conversion without reducing transmission capacity by storing data remaining without bus width conversion being performed that occurs when filling the buffer memory with input data transmitted from the parallel bus without making a free space to perform bus width conversion, in a buffer memory provided between the preceding stage bus switching unit and the following stage bus switching unit.

6. The semiconductor inspecting apparatus according to claim 1,
wherein by using ring-shaped bus switching processing for bus switching means for filling the buffer memory with input data from the parallel bus without making a free space, data capacity processed by each of buffer memories of unit width is even among the buffer memories.

7. The semiconductor inspecting apparatus according to claim 1,
wherein by using ring-shaped bus switching processing for bus switching means in the data transmission control unit, data capacity read from buffer memories of unit width is even among the buffer memories.

8. The semiconductor inspecting apparatus according to claim 1,
wherein by using ring-shaped bus switching processing for bus switching means for filling the buffer memory with input data from the serial lanes without making a free space, data capacity processed by each of buffer memories of unit width is even among the buffer memories.

9. The semiconductor inspecting apparatus according to claim 1,
wherein by using ring-shaped bus switching processing for bus switching means for filling data read from the buffer memory to a parallel bus width specified by the first parameter without making a free space, data capacity read from each of buffer memories of unit width is even among the buffer memories.

10. The semiconductor inspecting apparatus according to claim 1,
wherein the bus switching means for filling data read from the buffer memory to the width of the number of serial lanes specified by the second parameter without making a free space, when a gap occurs in transmission data when a serial transmission frame is formed with data read from the buffer memory after bus width conversion, performs padding processing of generating special blank data for padding the gap to form the serial transmission frame.

11. The semiconductor inspecting apparatus according to claim 1, comprising a data transmission control apparatus of a transmission side and a data transmission control apparatus of a reception side that include plural parallel ports, and transmitting various data generated within the semiconductor inspecting apparatus that is inputted to the plural parallel ports, in a single collected data transmission system.

12. A semiconductor inspecting apparatus, comprising:
a large-capacity data generation apparatus such as an image sensor that images a wafer surface;
a data transmission apparatus including at least one of a data transmission control unit that controls the transmission of data generated by the large-capacity data generation apparatus and a data reception control unit that controls the reception of the data; and
a processing apparatus that processes the transmitted data,
wherein the data transmission control unit includes:
a buffer memory having a parallel bus clock of arbitrary speed and a serial bus clock of arbitrary speed matched to the greater of parallel bus width having a parallel bus of arbitrary width driven by the parallel bus clock and specified by a first parameter and the width of the number of serial lanes having the serial lane of arbitrary number driven by the serial bus clock and specified by a second parameter;
bus switching means for filling the buffer memory with input data from the parallel bus without making a free space;
bus switching means for filling data read from the buffer memory to the width of the arbitrary number of serial lanes without making a free space; and
means for forming a serial transmission frame with data read from the buffer memory,
wherein the data reception control unit includes:
a buffer memory matched to the greater of parallel bus width having a parallel bus of arbitrary width driven by the parallel bus clock and specified by a first parameter and the width of the number of serial lanes having the serial lane of arbitrary number driven by the serial bus clock and specified by a second parameter;
means for receiving reception frame data from the serial lane and disassembles a reception frame;
bus switching means for filling the buffer memory with input data without making a free space; and
bus switching means for fills the parallel bus of arbitrary width with data read from the buffer memory without making a free space,
wherein the data transmission control unit and the data reception control unit each are constituted by circuit modules, and
wherein each of the circuit modules has a program that has the first parameter, the second parameter, and a terminal capable of inputting the use of transmission control and reception control, adjusts parallel width and the width of the number of serial lanes by the first parameter and the second parameter inputted from the terminal, respectively, according to the use of transmission control and reception control inputted from the terminal, determines whether the modules are required, or combines them, and automatically customizes the respective apparatuses of the data transmission control unit and the data reception control unit.

* * * * *